United States Patent
Hassdenteufel

(10) Patent No.: US 6,416,539 B1
(45) Date of Patent: Jul. 9, 2002

(54) CONTROLLED LENGTH INTRALUMINAL IMPLANT

(75) Inventor: Hans Hassdenteufel, Mainz (DE)

(73) Assignee: Medex, Inc., Dublin, OH (US)

( * ) Notice: Subject to any disclaimer, the term of this patent is extended or adjusted under 35 U.S.C. 154(b) by 0 days.

(21) Appl. No.: 09/462,032

(22) PCT Filed: Jun. 29, 1998

(86) PCT No.: PCT/EP98/03972

§ 371 (c)(1),
(2), (4) Date: Dec. 29, 1999

(87) PCT Pub. No.: WO99/01086

PCT Pub. Date: Jan. 14, 1999

(30) Foreign Application Priority Data

Jun. 30, 1997 (EP) .............................. 97810417

(51) Int. Cl.$^7$ .................................................. A61F 2/06
(52) U.S. Cl. ...................................... 623/1.15; 623/1.16
(58) Field of Search ............................. 623/1.15, 1.17, 623/1.31, 1.16, 23.7

(56) References Cited

U.S. PATENT DOCUMENTS

| | | |
|---|---|---|
| 2,701,559 A | 2/1955 | Cooper |
| 3,657,744 A | 4/1972 | Ersek |
| 4,018,230 A | 4/1977 | Ochiai et al. |
| 4,140,126 A | 2/1979 | Choudhury |
| 4,299,226 A | 11/1981 | Banka |
| 4,328,811 A | 5/1982 | Fogarty |
| 4,338,942 A | 7/1982 | Fogarty |
| 4,403,612 A | 9/1983 | Fogarty |
| 4,503,569 A | 3/1985 | Dotter |
| 4,560,374 A | 12/1985 | Hammerslag |
| 4,580,568 A | 4/1986 | Gianturco |
| 4,733,665 A | 3/1988 | Palmaz |
| 4,739,762 A | 4/1988 | Palmaz |
| 4,776,337 A | 10/1988 | Palmaz |
| 4,856,516 A | 8/1989 | Hillstead |
| 5,041,126 A | 8/1991 | Gianturco |
| 5,100,429 A | 3/1992 | Sinofsky et al. |

(List continued on next page.)

FOREIGN PATENT DOCUMENTS

| | | | |
|---|---|---|---|
| DE | 4432938 A1 | 3/1995 | |
| DE | 4418336 A1 | 11/1995 | |
| DE | 29702671 U1 | 5/1997 | |
| DE | 0970664 A3 * | 6/1999 | ................ 623/1.15 |
| EP | 0378151 A2 | 7/1990 | |
| EP | 0221570 B1 | 1/1991 | |
| EP | 0312852 B1 | 8/1991 | |
| EP | 0282175 B1 | 11/1991 | |
| EP | 0335341 | 3/1992 | |
| EP | 0565251 A1 | 10/1993 | |
| EP | 0423916 B1 | 4/1995 | |
| EP | 0421729 B1 | 1/1996 | |
| EP | 0480667 B1 | 3/1996 | |
| EP | 0744164 A1 | 11/1996 | |
| WO | WO93/13825 | 7/1993 | |
| WO | WO96/03092 | 2/1996 | |
| WO | WO96/26689 | 9/1996 | |

*Primary Examiner*—David H. Willse
*Assistant Examiner*—Suzette Jackson
(74) *Attorney, Agent, or Firm*—Wood, Herron & Evans LLP

(57) ABSTRACT

The invention relates to an intraluminal implant (1) manufactured from a seamless thin walled metal tube. The inventive device consists of a large number of expandable rings 92). The adjacent rings (2) are connected to each other by one of two extendible rods (4). Each radially expandable ring (2) can consists of one or several bands (3) which can be enlarged. The adjacent bands (3) are connected each other by means of rods (5) extending in an axial direction. The stent is highly flexible; as a result, its longitudinal extension remains practically unchanged when it is enlarged.

18 Claims, 2 Drawing Sheets

U.S. PATENT DOCUMENTS

| | | |
|---|---|---|
| 5,102,417 A | 4/1992 | Palmaz |
| 5,133,732 A | 7/1992 | Wiktor |
| 5,135,536 A | 8/1992 | Hillstead |
| 5,139,480 A | 8/1992 | Hickle et al. |
| 5,158,548 A | 10/1992 | Lau et al. |
| 5,195,984 A | 3/1993 | Schatz |
| 5,201,901 A | 4/1993 | Harada et al. |
| 5,221,261 A | 6/1993 | Termin et al. |
| 5,234,456 A | 8/1993 | Silvestrini |
| 5,242,399 A | 9/1993 | Lau et al. |
| 5,282,823 A | 2/1994 | Schwartz et al. |
| 5,314,444 A | 5/1994 | Gianturco |
| 5,314,472 A | 5/1994 | Fontaine |
| 5,356,423 A | 10/1994 | Tihon et al. |
| 5,378,239 A | 1/1995 | Termin et al. |
| 5,382,261 A | 1/1995 | Palmaz |
| 5,421,955 A | 6/1995 | Lau et al. |
| 5,443,496 A | 8/1995 | Schwartz et al. |
| 5,449,373 A | 9/1995 | Pinchasik et al. |
| 5,514,154 A | 5/1996 | Lau et al. |
| 5,527,354 A | 6/1996 | Fontaine et al. |
| 5,562,697 A | 10/1996 | Christiansen |
| 5,569,295 A | 10/1996 | Lam |
| 5,571,170 A | 11/1996 | Palmaz et al. |
| 5,571,173 A | 11/1996 | Parodi |
| 5,578,071 A | 11/1996 | Parodi |
| 5,591,197 A | 1/1997 | Orth et al. |
| 5,591,198 A | 1/1997 | Boyle et al. |
| 5,591,229 A | 1/1997 | Parodi |
| 5,591,230 A | 1/1997 | Horn et al. |
| 5,593,442 A | 1/1997 | Klein |
| 5,603,721 A | 2/1997 | Lau et al. |
| 5,632,771 A | 5/1997 | Boatman et al. |
| 5,643,208 A | 7/1997 | Parodi |
| 5,643,309 A | 7/1997 | Myler et al. |
| 5,649,952 A | 7/1997 | Lam |
| 5,667,523 A | 9/1997 | Bynon et al. |
| 5,683,453 A | 11/1997 | Palmaz |
| 5,695,516 A | 12/1997 | Fischell et al. |
| 5,697,971 A | 12/1997 | Fischell et al. |
| 5,707,386 A | 1/1998 | Schnepp-Pesch et al. |
| 5,713,949 A | 2/1998 | Jayaraman |
| 5,716,393 A | 2/1998 | Lindenberg et al. |
| 5,725,548 A | 3/1998 | Jayaraman |
| 5,728,158 A | 3/1998 | Lau et al. |
| 5,733,303 A | 3/1998 | Israel et al. |
| 5,735,893 A | 4/1998 | Lau et al. |
| 5,741,327 A | 4/1998 | Frantzen |
| 5,746,691 A | 5/1998 | Frantzen |
| 5,755,708 A | 5/1998 | Segal |
| 5,755,776 A | 5/1998 | Al-Saadon |
| 5,755,781 A | 5/1998 | Jayaraman |
| 5,759,192 A | 6/1998 | Saunders |
| 5,766,238 A | 6/1998 | Lau et al. |
| 5,776,161 A | 7/1998 | Globerman |
| 5,776,183 A | 7/1998 | Kanesaka et al. |
| 5,780,807 A | 7/1998 | Saunders |
| 5,807,404 A | 9/1998 | Richter |
| 5,810,868 A | 9/1998 | Lashinski et al. |
| 5,810,870 A | 9/1998 | Myers et al. |
| 5,810,872 A | 9/1998 | Kanesaka et al. |
| 5,817,126 A | 10/1998 | Imran |
| 5,836,964 A * | 11/1998 | Richter et al. ............. 623/1.15 |
| 5,843,117 A | 12/1998 | Alt et al. |
| 5,843,120 A | 12/1998 | Israel et al. |
| 5,843,164 A | 12/1998 | Frantzen et al. |
| 5,843,175 A | 12/1998 | Frantzen |
| 5,861,025 A | 1/1999 | Boudghene et al. |
| 5,861,032 A | 1/1999 | Subramaniam |
| 5,868,782 A | 2/1999 | Frantzen |
| 5,902,332 A | 5/1999 | Schatz |
| 5,916,264 A * | 6/1999 | Von Oepen et al. ........ 623/1.15 |
| 6,039,756 A * | 3/2000 | Jang ........................... 623/1.15 |
| 6,106,548 A * | 8/2000 | Roubin et al. ............. 623/1.15 |
| 6,123,721 A * | 9/2000 | Jang ........................... 623/1.15 |
| 6,129,755 A * | 10/2000 | Mathis et al. .............. 623/1.15 |
| 6,203,569 B1 * | 3/2001 | Wijay ........................ 623/1.15 |

\* cited by examiner

CONTROLLED LENGTH INTRALUMINAL IMPLANT

The invention relates to an intraluminal implant (stent) for dilating a blood vessel, as recited in the preamble of claim 1

Intraluminal implants for dilating blood vessels having a first diameter and being adapted to be expanded so as to have a second diameter once placed inside the blood vessel have been known since 1978. The oldest implants are simple helically wound wire coils which are introduced in a radially compressed condition and released when in place at the desired location in the lumen so that they can expand radially and, at the same time, push the wall of the vessel radially outwardly. The application of spring-elastic stents was replaced by plastically deformable implants as balloon-tipped catheters became more widely used.

There are essentially three basic types of these implants. Structures having a wound endless wire are known from EP-A-0 282 175, EP-A-0 312 852, EP-A-0 378 151 or U.S. Pat. No. 5,133,732, U.S. Pat. No. 5,135,536 and U.S. Pat. No. 5,562,697 or DE-A-44 32 938, just to name a few. These stents do not have a very stable shape and, therefore, are difficult to mount on a balloon-tipped catheter.

By far the greatest number of intraluminal implants consist of a kind of braided fabric made from a plurality of wires of extremely complicated form and partly reinforced by spot welding. A selection of such stents may be gathered from EP-A-0 421 729, EP-A-0 423 916, EP-A-0 480 667, EP-A-0 565 251 or EP-A-0 744 164, just to name a few. From the point of view of manufacture, these implants are highly complicated and, consequently, also very expensive.

The stent of interest here is a plastically deformable intraluminal implant which is cut from a thin-walled tube by means of a laser so as to present a kind of mesh structure. It is a great advantage of such implants that their surface is an absolutely smooth cylinder when they are not in the widened or expanded state and, therefore, they can be mounted easily on a balloon-tipped catheter and they do not cause frictional drag worth mentioning when being introduced and displaced inside a vessel.

The remaining flat webs have a thickness which is much less than that of wires for braided stents of comparable diameter. The overall diameter of the implant thus is reduced accordingly and that permits its use in vessels having a small inner diameter or lumen.

A first embodiment according to EP-B-0 221 570 shows an implant consisting of a piece of tube in which rectangular recesses, all extending in axial direction, are formed by lasering. When not expanded, such an implant practically is flexurally stiff. As a consequence, the length of the stent is limited and that may make it necessary to place several stents next to one another. It is a delicate matter to position them so that they will not overlap and yet be almost contiguous. For this reason, a more advanced solution provides for the basically similarly shaped stent, to consist of a plurality of sections integrally joined each by a single straight web, such as specified in U.S. Pat. No. 5,195,984 from which the pre-characterizing part of claim 1 starts. The flexibility of this solution corresponds to a coarse link chain and has a tendency to buckle.

All the known intraluminal implants made from a tube suffer contraction in axial direction when their diameter is widened. This contraction is difficult to estimate although it is directly related to the expansion. That makes it difficult for the physician to make the right choice of the stent needed and to position it correctly.

This holds also true for a conventional stent (WO 97/26689) comprising several rings of meandering webs of material. The outermost rings of, e. g., six adjacent rings may be longer than the inner rings in between. The rings are interconnected each by three straight webs extending obliquely with regard to the center axis of the rings. The rings are offset in angular direction to each other by 120°. Another similarly formed stent (DE 44 18 336 A1) has provided, parallel to the axis, short interconnecting webs between adjacent rings. Finally, a stent is known (DE 297 02 671) the rings of which consist of a plurality of adjacent, hair-pin shaped strands which form a tightly meandering web of material. The rings are interconnected by a plurality of web ogives having peak and bottom. All these known stents have a reduced axial flexibility. When expanding the stents, there is a pronounced reduction of the total length, because the interconnecting webs between the rings are not or practically not stretched. The axial or frictional force needed therefor cannot be exerted by a balloon-tipped catheter during expansion.

It is the object of the invention to improve a luminal implant (stent) of the kind mentioned just above which after insertion into a vessel is plastically expanded in the radial direction, such that it is flexible in axial direction in the non-expanded state and which, however, does not kink or upset and does not display any relevant change in length when being expanded. After expansion, it should possess sufficient elastic properties so as to conform to the deformations of the coronary vessels during heartbeat.

This object is met by an implant with the characterizing features of claim 1. Further advantageous modifications may be gathered from the dependent claims.

The drawing is a greatly simplified representation of a preferred embodiment of the subject matter of the invention.

FIG. 5 shows another modification in a developed view, just like

Figure 1:
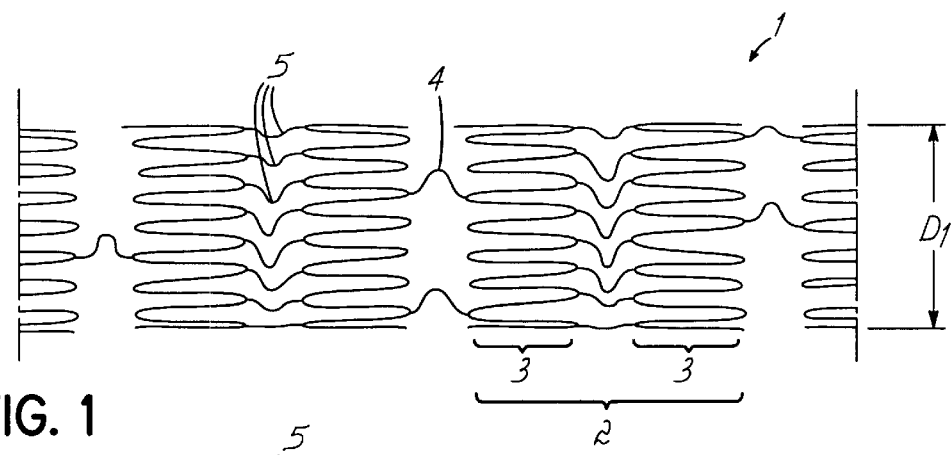
FIG. 1 is a side elevation of a section of a luminal implant in the non-expanded state in which it is introduced into a vessel.

The intraluminal implant according to the invention preferably is inserted in the blood circulation system, and again preferably into the coronary vessels. As already mentioned initially, the intraluminal implant of interest is made of a thin-walled seamless steel tube of surgical implant quality. Openings are cut out of this thin tube with a laser so that ultimately an article somewhat like a net or a net-like stocking is obtained. These remaining wall portions thus have the same thickness as the original wall thickness of the tube which was the starting tube. The wall thicknesses used for this purpose usually lie between 0.04 and 0.2 mm. The outer diameter of the seamless tube usually is between 1.0 and 5 mm. The width of the remaining wall portions or webs, of course, may vary as well.

In the drawing the intraluminal implant, also referred to as stent, is shown simplified in side elevation. All remaining webs of material are shown only as simple lines. In reality, of course, they have an area dimension, as explained above. For the sake of simplicity, however, this area dimension is not illustrated. In principle, those parts of the tubular material at the side remote from the viewer's side also would be visible because of the break-throughs caused by etching. Yet their presentation was omitted. Therefore, the side elevational view in fact is nothing but the view of half a tube.

In principle, the length of a stent may vary. On the one hand, it is dimensioned in accordance with the medical indication and, on the other hand, its minimum size and maximum length are determined by the balloon-tipped catheter used. The drawing depicts only a section of the intraluminal implant. The full transluminal implant 1 consists of a plurality of expandable rings 2, all of which present axial sections of the overall cylindrical stent. These rings or ring sections 2 are expandable. Expanding them in radial direction is effected, as is usual, by means of a balloon-tipped catheter. Each expandable ring 2 may consist of one or more hoops 3, the webs of which having a meandering configuration in a plane. Meandering webs are understood as being webs which may follow a zig-zag, sinuous, or any other such undulating path in the cylindrical surface they define. In the embodiment shown, these material webs take an undulating or meandering course. The cusps directed towards each other of adjacent hoops 3 of the same ring 2 are interconnected by webs 5. In the cylindrical surface, these webs are curved in axial direction, for instance so as to present an ogive. Thanks to these connections the individual hoops 3 are kept elastically and plastically deformable with respect to each other and yet they provide sufficient strength to prevent the highly filigreed structure from already becoming destroyed when it is placed on the dilator. Two adjacent rings 2 each likewise are interconnected by webs 4. To obtain the greatest possible flexibility of the stents, this connection is limited to the absolute minimum so that the axial flexibility of the stent will be optimized. Two webs 4 are provided between two adjacent rings. Preferably, however, two webs 4 will be applied. Yet they are not disposed diametrically opposite each other but rather include an obtuse angle, preferably of about 120°. The webs 4 between successive rings 2 are located so as to be offset by a certain angle each. Due to this arrangement the flexibility of the stent is approximately the same in every direction which deviates from the axial direction.

Figure 2:
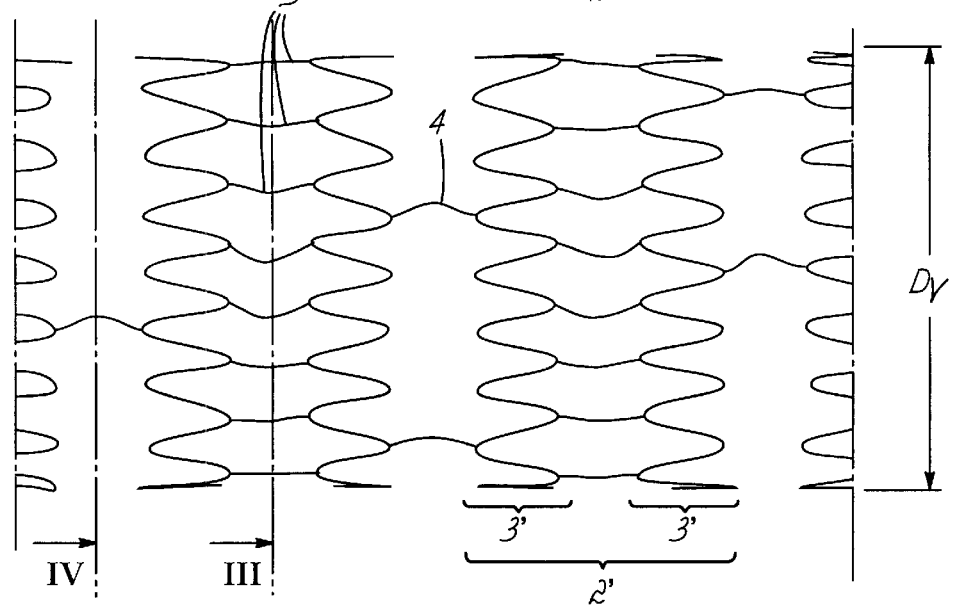
FIG. 2 shows the same section of the implant in expanded state.

While the section of the intraluminal implant according to FIG. 1 has a first diameter $D_1$, the same section in FIG. 2 has the expanded diameter $D_v$.

It may be seen in the drawing that practically the extension in axial direction has hardly changed during the widening. Although the length of the hoops 3 changes to the length of the hoops 31 during the expansion of the diameter from $D_i$ to $D_v$, this variation in length is relatively minimal and largely compensated by the stretching of the stretchable webs 5 between the hoops. The minor shortening of the hoops 3 causes a likewise minor shortening of the rings 2 in axial direction to a length 21. This variation in length is easily compensated by the two stretchable webs 4. The webs 4 also have the shape of an ogive. It proved to be advantageous to choose opposite directions for the ogive of the webs 4 between adjacent rings and the ogive of the webs 5 between adjacent hoops 3.

Figure 3:
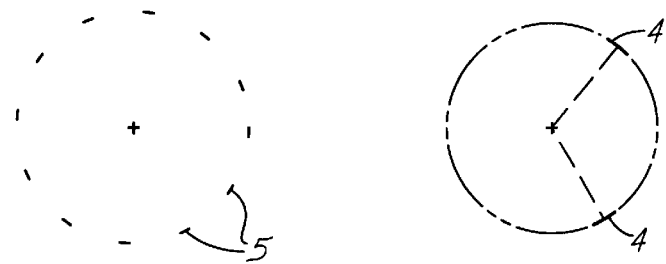
FIG. 3 is a vertical section perpendicular to the direction of the longitudinal axis along line III in FIG. 2.
Figure 4:
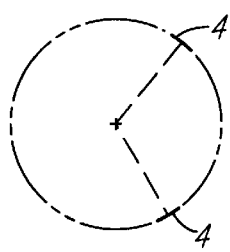
FIG. 4 is a similar section along line IV in FIG. 2.

The three-dimensional character of the implant 1 is lost with the form of presentation selected. FIGS. 3 and 4 which are vertical sections through the stent along lines III and IV, respectively, in FIG. 2 reveal the cylindrical configuration. In the case of the section along line III shown in FIG. 3, all the webs 5 between two adjacent hoops 4 of the same ring 2 are cut. The area dimension of the webs can be recognized somewhat exaggerated. In the case of the section according to FIG. 4, the two only stretchable webs 4 between two adjacent rings 2 are shown. These two webs 4 include an angle (. This angle is selected preferably between 90° and 180°. In the next gap area between two adjacent rings 2 these two webs 4 are offset by a certain angle, while the angle a is maintained. In one particular embodiment, angle (was set at 120° and the angle of offset of the webs of subsequent rings was set at 60°. Yet the choice of these angles can be varied.

Implants always are foreign matter in the body of a patient. For this reason, they should be as small as possible and as big as necessary. Since the overall length of the implant according to the invention practically does not change, the physician does not have to take into account a shortening factor of the implant when he applies the intraluminal implant according to the invention. As the stent becomes wider, the balloon of the balloon-tipped catheter expands most where it is confronted with the least resistance. In the present case that always is the region between two adjacent rings and in the zone of reduced contact at the periphery between two adjacent rings. Because of this fact, the rings and the hoops become positioned more or less strongly in axial direction when the balloon is blown up. Consequently, the axially occurring forces will cause more or less stretching of the webs 4 and 5, respectively, rather than just leading to displacement of the rings 2 or hoops 3 in the lumen or on the balloon of the catheter.

The expansion of the implant without a substantial change in length makes sure that the widening of the stent does not bring about any shifting of the rings which might cause injuries to the wall of the vessel.

The distinct great flexibility of the intraluminal implant in every direction that deviates from the axial one is so great that, even upon removal of the balloon-tipped catheter, the stent still can adapt subsequently to the course of the lumen, whereby the much feared kinks are avoided altogether. Especially where adjacent rings 2 are interconnected by two interconnecting webs 4, the flexibility of the stent is improved if the two webs are not disposed diametrically opposite each other but instead include an angle of 120°. for example.

Figure 5:
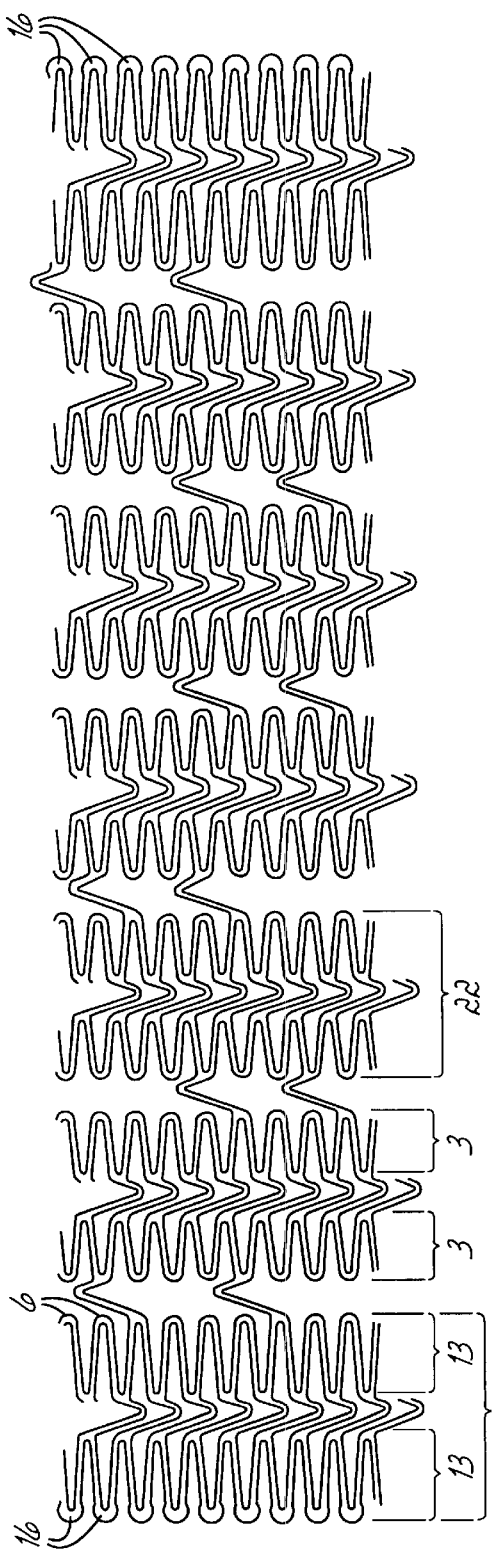
Figure 6:
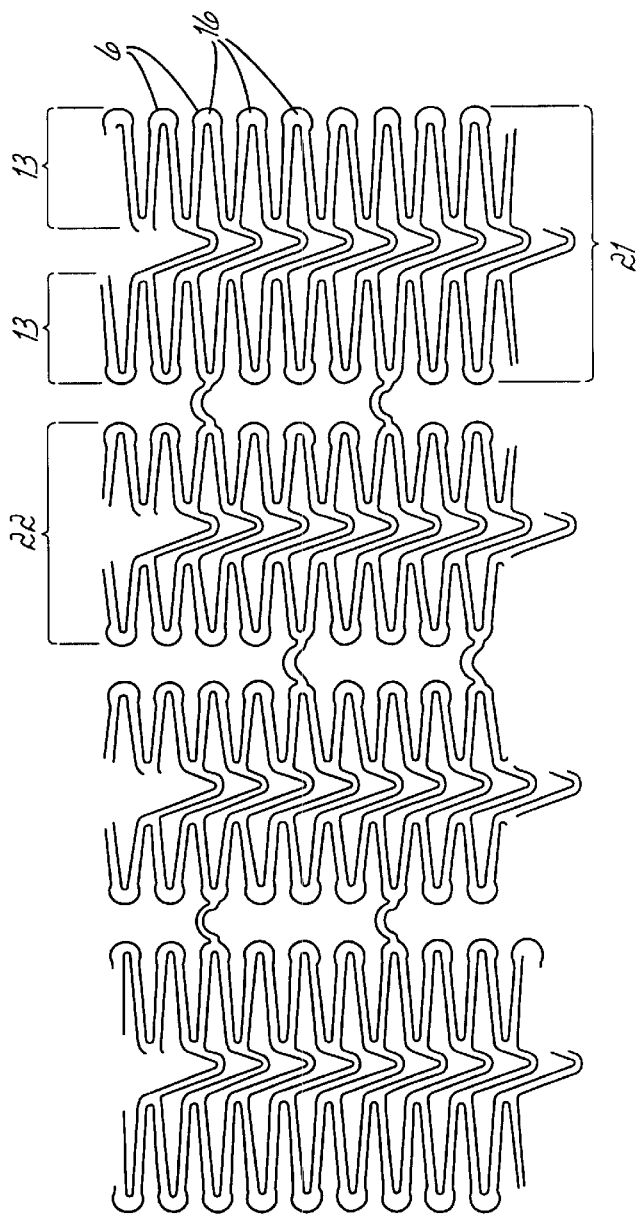
FIG. 6 shows a shorter stent in a developed view.

Two further modifications are illustrated in FIGS. 5 and 6. The stents shown in these figures are projections into the plane of the thin-walled intraluminal implants cut by means of a laser. It is a peculiarity of this embodiment that the length of the two outermost hoops 13 is greater than the length of the other hoops. Consequently, also the length of the two outermost rings 2 is greater than the length of the rings 22 in between. An inverted relationship exists between the length of the hoops or the length of the rings and the force required to expand them in radial direction to the desired size. This configuration is intended to ensure that the expanded implant will be in full engagement with the wall of the lumen also in the region of the outermost rings. The balloon of the balloon-tipped catheter, in principle, rather tends to bulge more in the middle than towards the edges. The configuration proposed here for the implant makes allowance for that fact. The width of the two respective outermost hoops 13 is selected to be even so great that some overcompensation is given so that the stent rather becomes widened more specifically in the marginal zones than in the middle.

When the meandering hoops or rings are expanded, the cusps 6 of the hoops 13 are pressed radially outwardly more strongly than the remaining portions. This results in some torsion, due to the deformation, and that counteracts the surface area contact between the cusps and the wall of the lumen. In order to avoid such an effect, especially as regards the outermost cusps 6, the cusps in this case are provided with wider portions 16. Then it may also make sense to provide wider portions for all the cusps 6, except those that are interconnected by webs 4, 5, particularly with Fa,n greater stents for use with greater lumen diameters. This solution is illustrated in FIG. 6. It follows from the above that the stent in accordance with the projection in FIG. 5 is a stent which becomes longer in axial direction than the one according to FIG. 6, yet the stent according to FIG. 5 is better suited for lumina of smaller extension when expanded. (FIG. 1)

What is claimed is:

1. An intraluminal implant for expanding a blood vessel comprising: a thin, tubular member, the thin tubular member being cut from a seamless, thin-walled metal tube in such a manner that two axially outer, and one or more axially inner, expandable rings of net-like or meander-like webs result, any two adjacent rings being interconnected with each other by only a pair of stretchable connecting webs curved in the axial direction of the tubular member with the stretchable connecting webs of the pair being angularly offset from each in a first radial direction at an angle of less than 180°, having a first diameter for the intraluminal conveyance of the tubular member, which may be expanded to a variable second diameter by exerting a radial, outwardly directed force from inside the tubular member, and which is inserted into the blood vessel by means of a balloon-tipped catheter and expanded therein, and wherein connecting web pairs succeeding each other in the axial direction being disposed angularly offset with respect to the preceding ones.

2. The intraluminal implant of claim 1 wherein the offset in the first radial direction is at an angle of 60° to 120°.

3. The intraluminal implant of claim 1, the connecting webs being arcuately curved.

4. The intraluminal implant of claim 1 wherein each expandable ring includes at least two hoops of meandering webs which hoops are connected to each other by a plurality of additional expandable connecting webs curved in the axial direction.

5. The intraluminal implant of claim 4, the connecting webs between adjacent rings being curved arcuately in a first direction and the additional connecting webs between adjacent hoops being curved arcuately in a second, opposite direction.

6. The intraluminal implant of claim 4 wherein each of the axially outermost rings has an axially outermost hoop, the axially outermost hoops having a greater axial length than any other of the hoops.

7. The intraluminal implant of claim 4 wherein the hoops forming the axially outermost rings are longer than the hoops forming the one or more axially inner rings.

8. The intraluminal implant of claim 1, each meandering web of the rings having a plurality of cusps.

9. The intraluminal implant of claim 8, wherein each of the axially outermost rings has a plurality of axially outermost cusps, at least the axially outermost cusps having wide flat portions.

10. An intraluminal implant for expanding a blood vessel comprising: a thin, tubular member, the thin tubular member being cut from a seamless, thin-walled metal tube in such a manner that two axially outer, and one or more axially inner, expandable rings of net-like or meander-like webs result, any two adjacent rings being interconnected with each other by only a pair of stretchable connecting webs curved in the axial direction of the tubular member with the stretchable connecting webs of the pair being disposed so that they are not diametrically opposed, having a first diameter for the intraluminal conveyance of the tubular member, which may be expanded to a variable second diameter by exerting a radial, outwardly directed force from inside the tubular member, and which is inserted into the blood vessel by means of a balloon-tipped catheter and expanded therein, and wherein connecting web pairs succeeding each other in the axial direction being disposed angularly offset with respect to the preceding ones.

11. The intraluminal implant of claim 10, the connecting webs being arcuately curved.

12. The intraluminal implant of claim 10 wherein each expandable ring includes at least two hoops of meandering webs which hoops are connected to each other by a plurality of additional expandable connecting webs curved in the axial direction.

13. The intraluminal implant of claim 12, the connecting webs between adjacent rings being curved arcuately in a first direction and the additional connecting webs between adjacent hoops being curved arcuately in a second, opposite direction.

14. The intraluminal implant of claim 12 wherein each of the axially outermost rings has an axially outermost hoop, the axially outermost hoops having a greater axial length than any other of the hoops.

15. The intraluminal implant of claim 12 wherein the hoops forming the axially outermost rings are longer than the hoops forming the one or more axially inner rings.

16. The intraluminal implant of claim 10, each meandering web of the rings having a plurality of cusps.

17. The intraluminal implant of claim 16, wherein each of the axially outermost rings has a plurality of axially outermost cusps, at least the axially outermost cusps having wide flat portions.

18. The intraluminal implant claim 10, the axially outermost rings having a greater axial length than the one or more axially inner rings.

* * * * *

UNITED STATES PATENT AND TRADEMARK OFFICE
CERTIFICATE OF CORRECTION

PATENT NO. : 6,416,539 B1
DATED : July 9, 2002
INVENTOR(S) : Hans Hassdenteufel

It is certified that error appears in the above-identified patent and that said Letters Patent is hereby corrected as shown below:

Column 3,
Line 34, please delete "include. an obtuse angle" and replace with -- include an obtuse angle --;
Line 47, please delete "$D_i$" and replace with -- $D_1$ --;

Column 4,
Line 37, please delete "angle of 120°. for" and replace with -- angle of 120° for --;

Column 5,
Line 2, please delete "with Fa,n greater stents" and replace with -- with greater stents --;
Line 20, please delete "offset from each in" and replace with -- offset from each other in --;

Column 6,
Line 51, please delete "implant claim 10" and replace with -- implant of claim 10 --;

Signed and Sealed this

Twenty-fifth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,416,539 B1                                             Page 1 of 1
DATED         : November 24, 2003
INVENTOR(S)   : Hans Hassdenteufel It is certified that error appears in the above-identified patent and that said Letters Patent is hereby corrected as shown below:

<u>Column 6,</u>
Line 54, please add claim 19 which reads -- The intraluminal implant of claim 1, the axially outermost rings having a greater axial length than the one or more axially inner rings. --

Signed and Sealed this

Tenth Day of February, 2004

JON W. DUDAS
*Acting Director of the United States Patent and Trademark Office*